(12) United States Patent
Wang et al.

(10) Patent No.: US 10,912,760 B1
(45) Date of Patent: Feb. 9, 2021

(54) METHOD OF INHIBITING CANCER METASTASIS

(71) Applicant: Chung Shan Medical University, Taichung (TW)

(72) Inventors: Chau-Jong Wang, Taichung (TW); Chia-Hung Hung, Taichung (TW)

(73) Assignee: Chung Shan Medical University, Taichung (TW)

( * ) Notice: Subject to any disclaimer, the term of this patent is extended or adjusted under 35 U.S.C. 154(b) by 0 days.

(21) Appl. No.: 16/536,320

(22) Filed: Aug. 9, 2019

(51) Int. Cl.
*A61K 31/4015* (2006.01)
*A61P 35/04* (2006.01)
*A61K 36/074* (2006.01)

(52) U.S. Cl.
CPC ........ *A61K 31/4015* (2013.01); *A61K 36/074* (2013.01); *A61P 35/04* (2018.01)

(58) Field of Classification Search
CPC .... A61P 35/04; A61K 31/4015; A61K 36/074
See application file for complete search history.

(56) References Cited

U.S. PATENT DOCUMENTS

2010/0210865 A1* 8/2010 Sheu .................. A61P 9/08
560/55
2017/0189417 A1* 7/2017 Chen .................. A61K 31/575

OTHER PUBLICATIONS

Lin et al., "Inhibition of cell survival, cell cycle progression, tumor growth and cyclooxygenase-2 activity in MDA-MB-231 breast cancer cells by camphorataimide B." Eur. J. Pharmacol. Apr. 5, 2012;680(1-3):8-15. PMID: 22329896. (Year: 2012).*

* cited by examiner

*Primary Examiner* — Theodore R. Howell
(74) *Attorney, Agent, or Firm* — Hannah Tien

(57) ABSTRACT

The present invention relates to a method for inhibiting a cancer metastasis in a subject in need thereof, comprising administering to said subject a cancer metastasis-inhibiting effective amount of: Camphorataimide B; or a composition comprising Camphorataimide B and a pharmaceutically acceptable adjuvant, vehicle, or carrier.

4 Claims, 14 Drawing Sheets
(6 of 14 Drawing Sheet(s) Filed in Color)

Liver metastasis

Abdominal metastasis

METHOD OF INHIBITING CANCER METASTASIS

FIELD OF THE INVENTION

The present invention relates to a method for inhibiting a cancer metastasis in a subject in need thereof.

BACKGROUND OF THE INVENTION

In order to treat cancers, there has been adopted chemical therapy using various anticancer agents, immunotherapy for promoting the production of antibodies against cancer cells, surgical therapy for extracting cancer cells, radiotherapy for killing cancer cells by irradiation, etc. However, as these therapies have been developed, the surgical operations or radiotherapy technically suffer their limits, and cannot effectively inhibit the metastasis of the cancers. On the other hand, although the chemical therapy directly acts upon the cancer cells with use of the anticancer agents, many of the anticancer agents then cause harmful side effects even upon normal cells of a host. Therefore, the chemical therapy is not necessarily effective for the metastasis of the cancer. Further, no excellent effects against the metastasis of the cancers have been seen in the case of the immunotherapy which is to treat the cancer. Although the therapeutic effects against original cancers have been largely enhanced, not a few patients become dead by metastasized cancers provoked by the metastasis of cancer cells, even if the original cancers are completely cured. In order to inhibit the metastasis of the cancers, there has strongly demanded development of medicines for inhibiting the metastasis of cancer cells.

Camphorataimide B, a maleimide in mycelium of *Antrodia camphorata*, has the structure as follows:

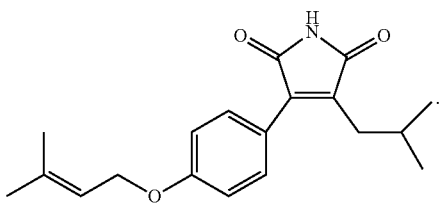 [SMILES: CC(C)=CCOc1ccc(C2=C(CC(C)C)C(=O)NC2=O)cc1]

It has been reported that Camphorataimide B can inhibit tumor growth in breast cancer cells; however, the ordinary skills in the art understand that an anti-cancer agent is not necessarily effective for the metastasis of the cancer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

SUMMARY OF THE INVENTION

Figure 1A:
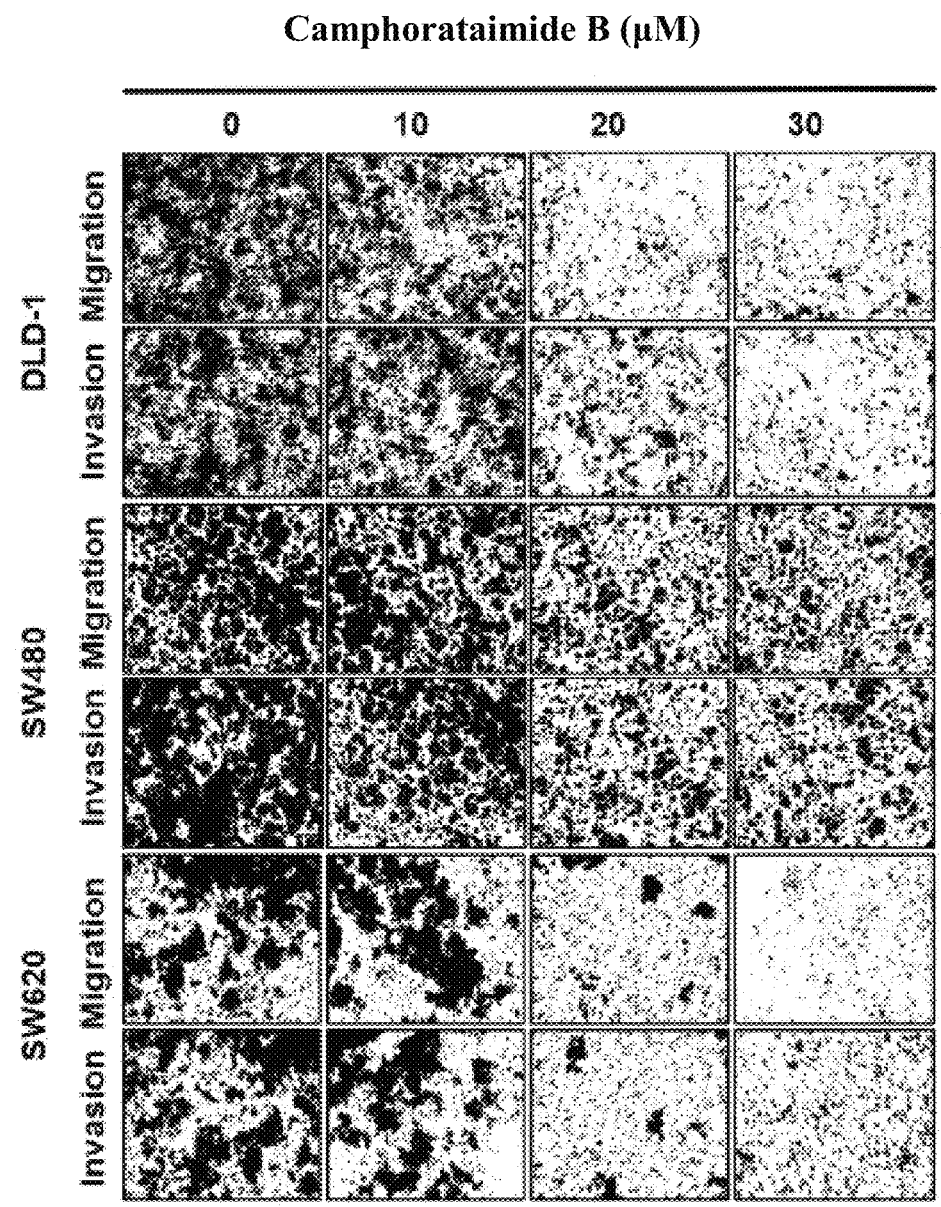
FIG. 1A: Effect of Camphorataimide B on migration and invasion of colon cancer cells. For migration assay, three colon cancer cells (DLD-1, SW480 and SW620) were pretreated with the indicated concentrations of Camphorataimide B for 24 hours, seeded onto transwell inserts, and then incubated for 12 hours. For invasion assay, the three colon cancer cells were pretreated with the indicated concentrations of Camphorataimide B for 24 hours, seeded onto Matrigel coated transwell inserts, and then incubated for 16 hours. After the treatments, numbers of cell on the lower surface membrane were stained, photographed and counted for quantitation of migrated and invaded cells.

The present invention relates to a method for inhibiting a cancer metastasis in a subject in need thereof, comprising administering to said subject a cancer metastasis-inhibiting effective amount of: Camphorataimide B; or a composition comprising Camphorataimide B and a pharmaceutically acceptable adjuvant, vehicle, or carrier.

DETAILED DESCRIPTION OF THE INVENTION

Whether Camphorataimde B inhibits the motility and invasiveness of three colon cancer cells (DLD-1, SW480 and SW620) is investigated in the present invention. In addition, growing in anchorage-independent manner is also an important marker for metastatic carcinoma. Therefore, capability of colony formation and adhesion to extracellular matrix of the three colon cancer cells exposed to Camphorataimide B is also determined. Formation of lamellipodia, stress fiber and filopodia comprising actin cytoskeleton plays a central role in cell adhesion and migration, therefore, effects of Camphorataimide B on structure of F-actin in the three colon cancer cells are also investigated. The results demonstrate that Camphorataimde B suppresses adhesion, migration and invasion of colon cancer cells in vitro. Therefore, ex vivo and in vivo effects of Camphorataimide B treatments on tumorigenesis and metastasis by colon cancer cells are further explored. The results demonstrate that Camphorataimide B suppresses liver and abdominal metastasis of DLD-1 cells in ex vivo and in vivo xenograft mice model. According to the above, the present invention demonstrates that Camphorataimide B is an effective cancer metastasis-inhibiting agent.

The term "Camphorataimide B" used herein can be used interchangeably with "Antrodin B". The structure of Camphorataimide B is shown as follows:

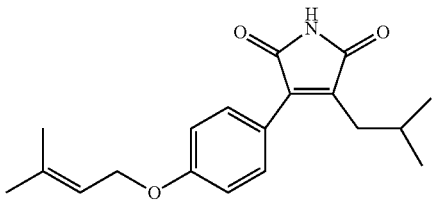 [SMILES: CC(C)=CCOc1ccc(C2=C(CC(C)C)C(=O)NC2=O)cc1]

The term "colorectal cancer" used herein refers to a cancer that starts in the colon or the rectum, which is also known as "colon cancer", "rectal cancer", or "bowel cancer", depending on where it starts. Colon cancer and rectal cancer are often grouped together because they have many features in common.

Therefore, the present invention provides a method for inhibiting a cancer metastasis in a subject in need thereof, comprising administering to said subject a cancer metastasis-inhibiting effective amount of: Camphorataimide B; or a composition comprising Camphorataimide B and a pharmaceutically acceptable adjuvant, vehicle, or carrier. In an embodiment, the cancer is colorectal cancer. In an embodiment, the subject is a mammal, such as a human.

As pharmaceutical preparations of the present invention, oral administration preparations such as tablets, capsules, powders, etc., percutaneous absorption preparations such as suppository, vaginal suppository, etc, and injection preparations for subcutaneous injections, intraperitoneal injections, intraveneous injections, etc. may be recited. The oral administration preparations are most preferable for the purpose of preventing diseases, whereas the injection preparations are most preferable for the purpose of emergency. The oral administration preparations, percutaneous absorption preparations and injection preparations may be formulated according to ordinary medicine-formulating processes.

EXAMPLES

The examples below are non-limiting and are merely representative of various aspects and features of the present invention.

Example 1

Materials and Methods
Cell Migration and Invasion Assay

Cells were pretreated with Camphorataimide B for 24 hours, harvested and then seeded on to 24-well cell culture inserts (8 μm pore size, Millipore). A 24h-lung metastatic colon cancer cell conditional medium was used as a chemoattractant placed in the lower compartment of the plate and incubated for 12 hours. The cells that migrated to the lower surface of the insert were fixed and stained with Giemsa reagent (Sigma-Aldrich). The stained cells were photographed and quantified form five random fields under microscopic examination. For the invasion assay, the culture inserts were pre-coated with 100 μL of Matrigel (20X dilution in PBS) and air-dried overnight. Cells were seeded onto the coated culture insert and incubated for 16 hours. Cells invaded into the lower surface of the insert were quantitated as described earlier.

Cell Adhesion Assay

Cells were incubated with serial concentration of Camphorataimide B in a complete medium for 24 hours, transferred in to 12-well Matrigel coated plates (105 cells per well), and incubated at 37° C. for 8 hours. After the incubation, non-adherent cells were removed by PBS washing and the attached cells were photographed and quantitated using a cell counter.

Soft Agar Assay

Cells suspended in agarose medium (10% FBS and 0.3 agarose in medium) containing serial concentrations of Camphorataimide B were plated onto 6-well plate which was pre-coated with a layer of solidified agarose (10% FBS and 0.6% agarose in medium), and then incubated at 37° C. in a humidified atmosphere containing 5% $CO_2$ for 1 week. At the end of incubation, cell colonies were fixed, stained with crystal violet, and then photographed using Nikon Eclipse TE2000-U microscope equipped with a Nikon Digital Camera DXM1200 and those colonies with size greater than 0.1 mm were counted.

Immunofluorescence Staining

Adherent cells were fixed on the glass slides using 4% ice-cold formaldehyde and reacted with blocking buffer and 0.5% Triton X-100 for 1 hour at room temperature. The reacted cells were incubated with primary antibodies overnight at 4° C. The bound primary antibodies were detected using Alexa Fluor-labeled secondary antibody (Jackson ImmunoResearch Laboratories, West Grove, Pa., USA). Alexa Fluor-conjugated phalloidin (Cell Signaling) was used for detection of polymerized F-actin microfilaments. Fluorescence image was acquired by using a laser scanning confocal microscope system (Zeiss 510 meta, Zeiss, Oberkochen, Germany).

Histopathological Examination

The livers were collected, cut into small pieces, fixed in 10% buffered neutral formalin, and embedded in paraffin. Sections were cut at a thickness of 3-5 μm and stained with hematoxylin and eosin. The histopathological changes, including cell morphology and cellular lipid vesicles, were examined by light microscopy (400×).

Human Colon Cancer Xenograft Mouse Model

Male Balb/c nude mice aged four weeks were purchased from National Laboratory Animal Center of Taiwan (Taipei City, Taiwan) and maintained under supervision of the Institutional Animal Care and Use Committee at Chung Shan Medical University. After one-week maintenance, mice were randomly divided in to three groups (control, Luc-DLD-1, and Luc-DLD-1+Camphorataimide B), each group contained ten mice. For liver metastatic ex vivo model, tumor implantation was performed by spleen and intraperitoneal injection of Luc-DLD-1 (Luciferase expressing-DLD-1) cells with or without Camphorataimide B treatment (30 μm for 24 hours). For in vivo model, $2\times10^6$ Luc-DLD-1 cells were suspended in 20 μL phosphate buffered saline and injected into the spleen of 5-week-old male Balb/c nude mice. After one week, mice were orally administrated with 10 and 20 mg/kg Camphorataimide B every three days. The liver metastasis burden was monitored weekly by bioluminescence imaging (BLI). Mice were anesthetized each time and given intraperitoneal injection of luciferin (150 μgig body weight prepared in PBS). After 10-15 minutes, BLI were captured with a charge-coupled camera. 35 days later, the mice were sacrificed and tumor tissues were excised and collected for analysis of tumor weight and number. The metastatic nodules of the visible tumor on the liver were identified by histochemical analysis.

Statistical Analysis

The data represented the mean±SD form three independent experiments except where indicated. The student's test was used to analyze the significance of difference. Results with $p<0.05$ were considered statistically significant.

Results

Camphorataimide B Suppressed Adhesion, Migration and Invasion of Colon Cancer Cells.

Figure 1B:
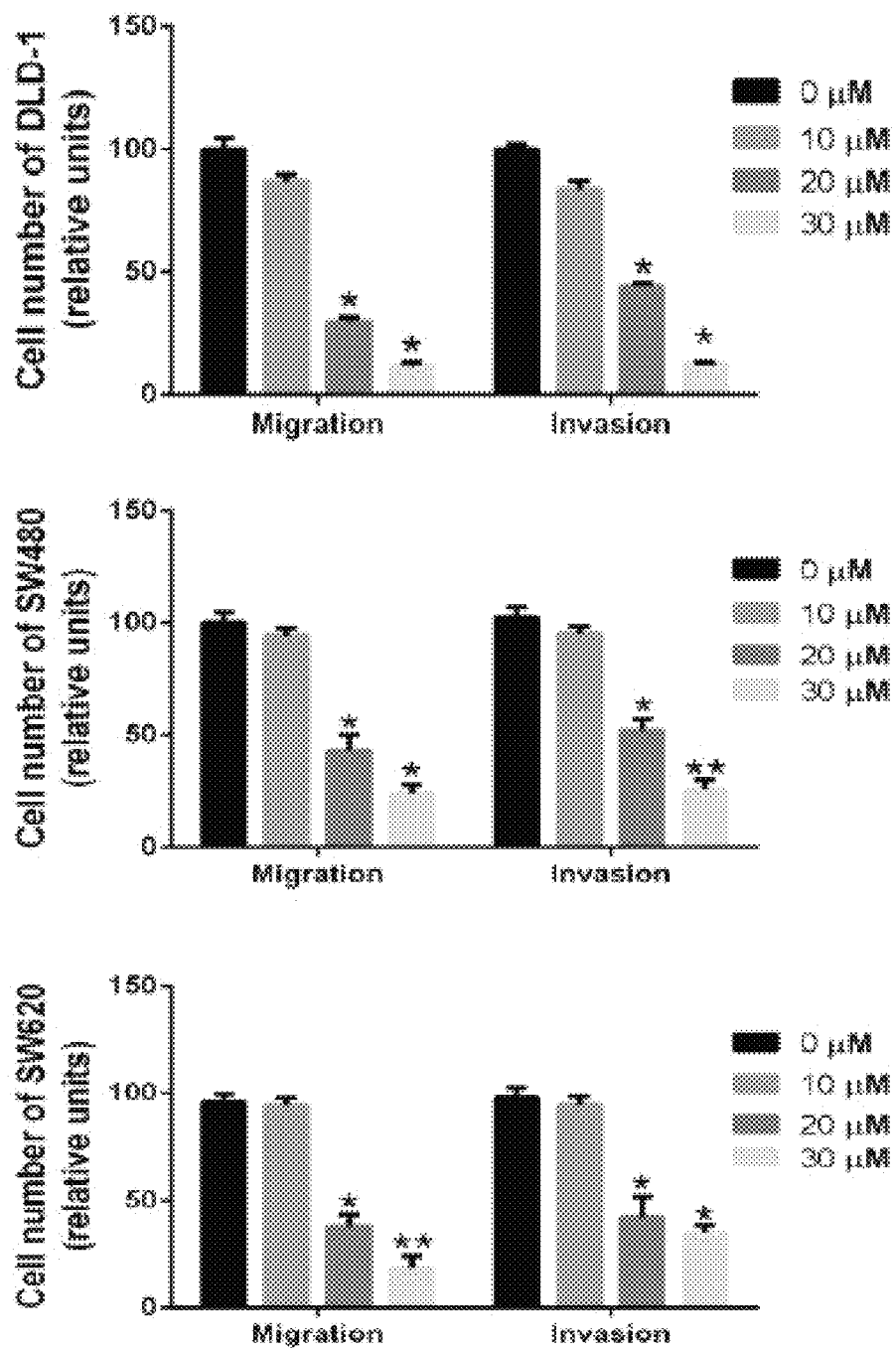
FIG. 1B: Quantitation of effect of Camphorataimide B on migration and invasion of colon cancer cells. Quantitative results were presented as means±SD. Three independent experiments were performed for statistical analysis. * and ** represented P<0.01 and P<0.001 as compared to control, respectively.
Figure 1C:
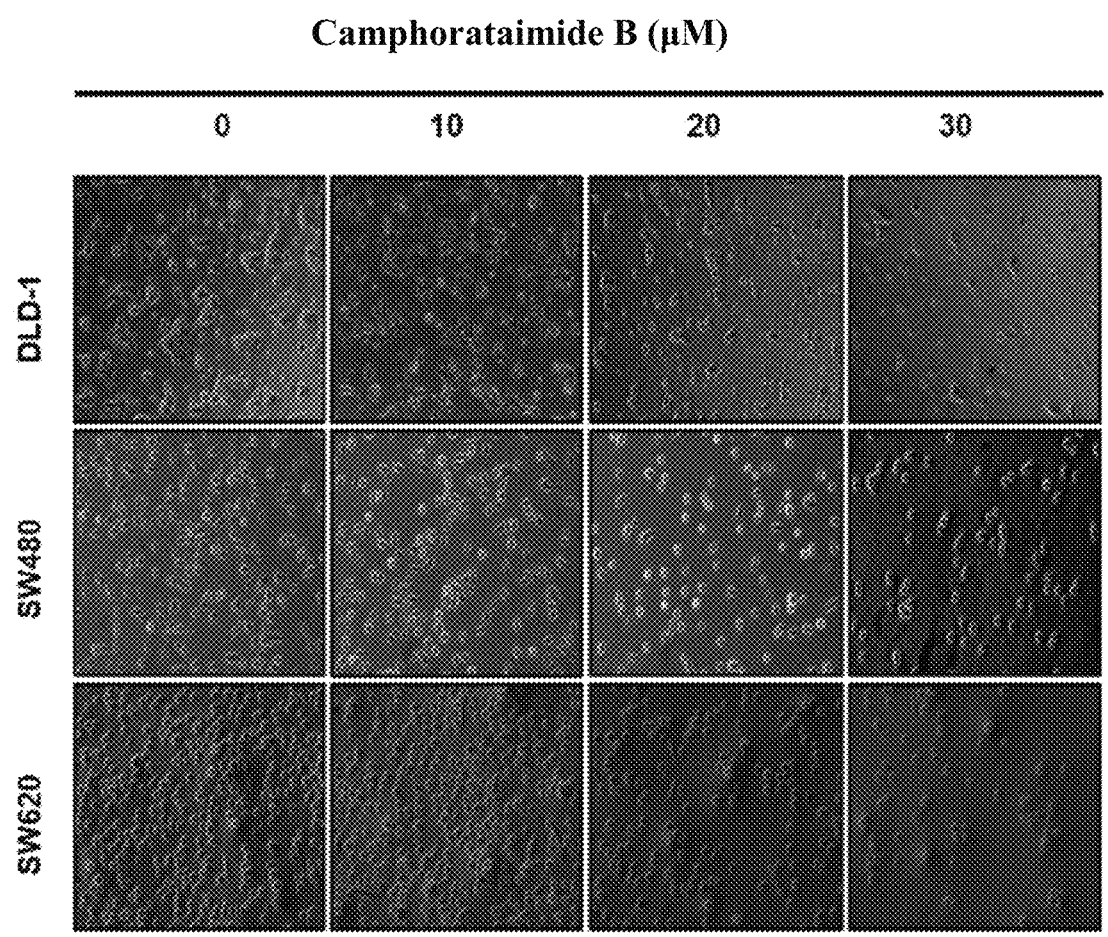
FIG. 1C: Effect of Camphorataimide B on adhesion of colon cancer cells. The three colon cancer cells were pretreated with the indicated concentrations of Camphorataimide B for 24 hours, seeded on a matrix coated monolayer dish, and then incubated for 8 hours. After washing with PBS, the attached cells were photographed and quantitated.
Figure 1D:
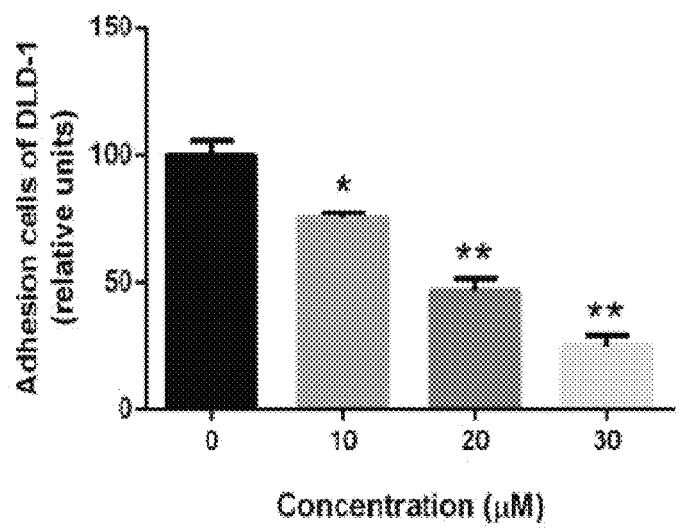
FIG. 1D: Quantitation of effect of Camphorataimide B on adhesion of colon cancer cells. Quantitative results were presented as means±SD. Three independent experiments were performed for statistical analysis. * and ** represented P<0.01 and P<0.001 as compared to control, respectively.
Figure 1D:
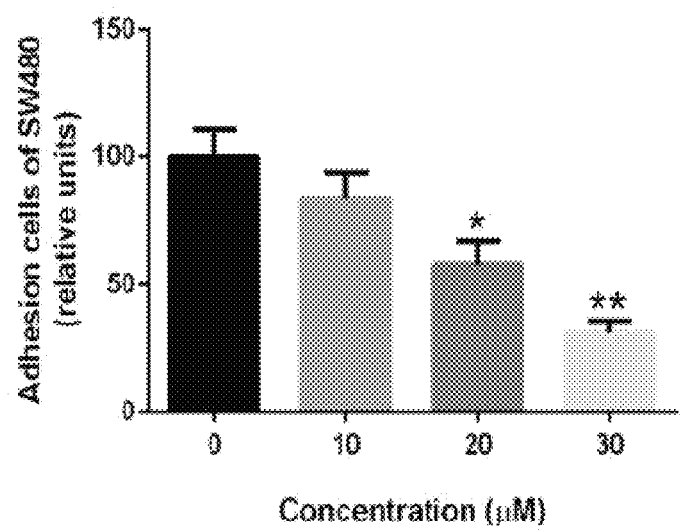
Figure 1D:
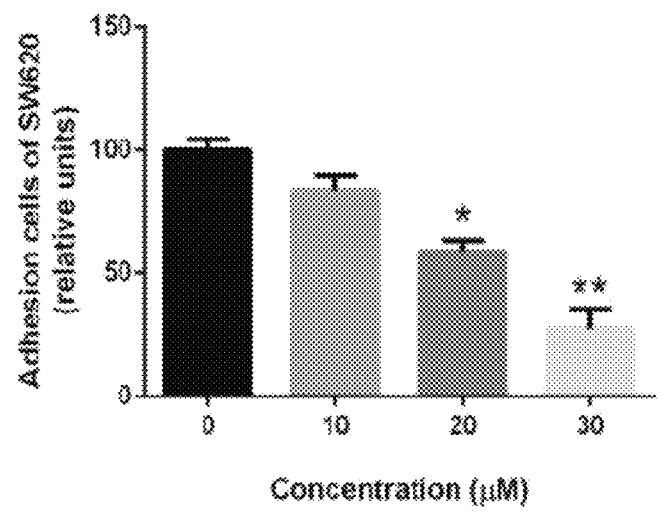
Figure 1E:
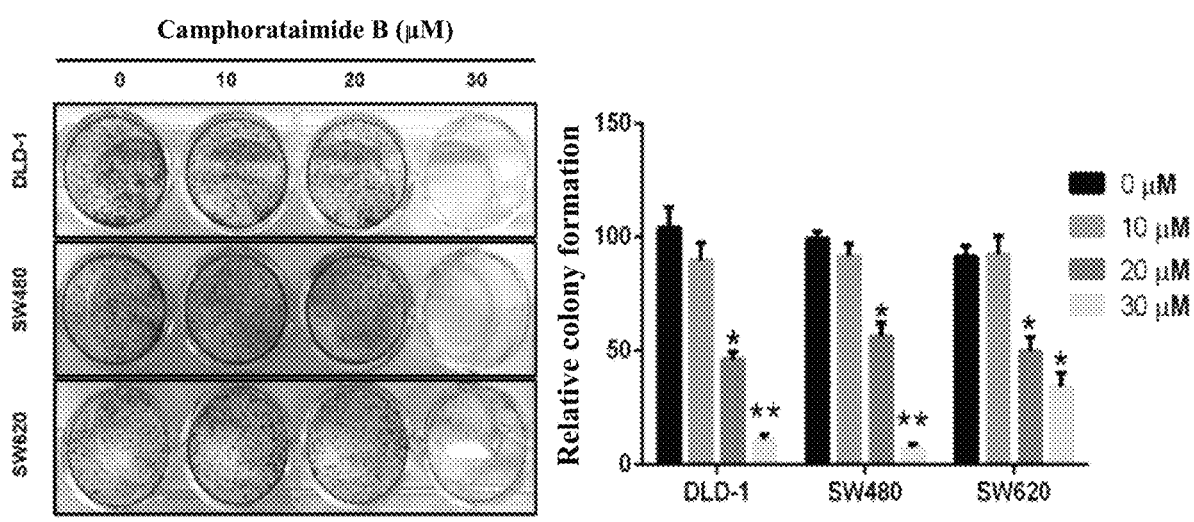
FIG. 1E: Effect of Camphorataimide B on colony formation of colon cancer cells. The three colon cancer cells were pretreated with indicated concentration of Camphorataimide B for 24 hours, seeded on soft agar plates, and then incubated for one week. After the treatments, the number of colonies was quantitated. Quantitative results were presented as means±SD. Three independent experiments were performed for statistical analysis. * and ** represented P<0.01 and P<0.001 as compared to control, respectively.
Figure 1F:
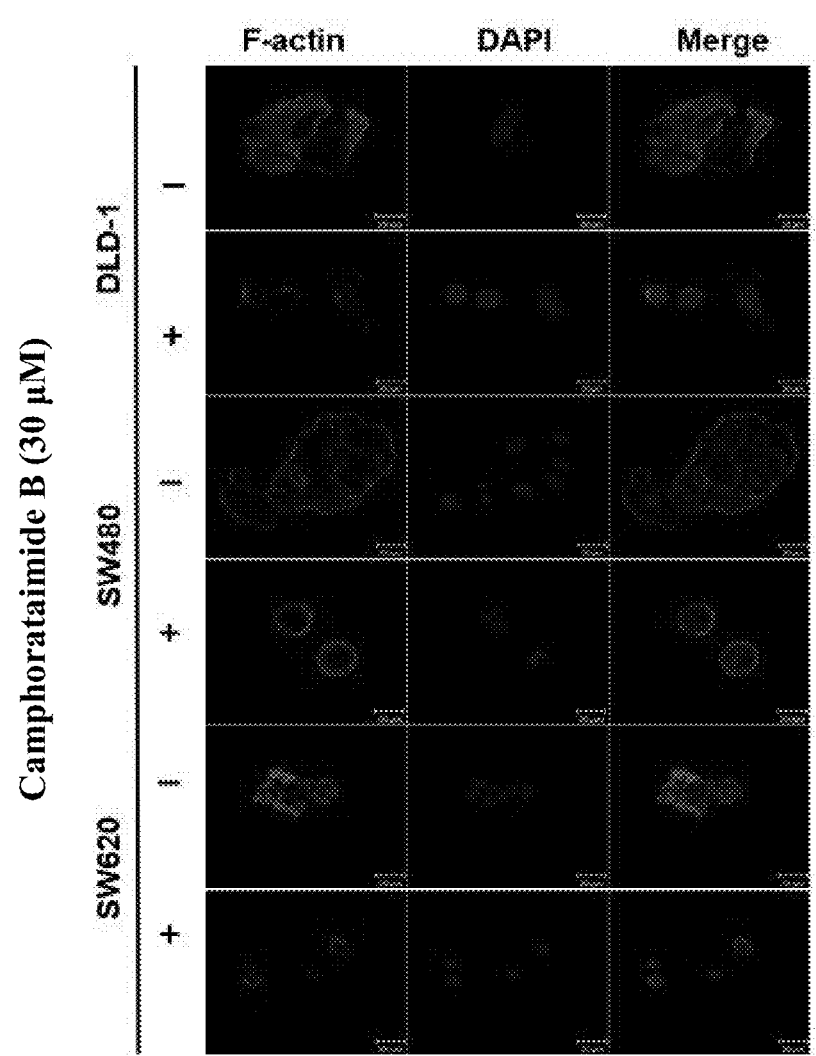
FIG. 1F: Effect of Camphorataimide B on cytoskeleton structure of colon cancer cells. The treated cells were seeded on a matrix-coated dish, and then F-actin (red) was detected by immunofluorescence staining, while the nuclei (blue) were detected by DAPI staining. Fluorescent images were acquired by using confocal microscopy. Scale bars, 20 gym. Similar images were observed in three independent experiments.

As shown in FIGS. 1A and 1B, Camphorataimide B treatments dose-dependently inhibited migration and invasiveness of colon cancer cells, and inhibition of migration and invasiveness by 20 and 30 μM Camphorataimide B was significant ($P<0.01$ as compared to control). In addition, capability of colony formation and adhesion to extracellular matrix of colon cancer cells exposed to Camphorataimide B was also determined. As shown in FIGS. 1C-1E, both adherent cell (FIGS. 1C and 1D) and colony numbers (FIG. 1E) were significantly reduced in response to Camphorataimide B treatments. Effects of Camphorataimide B on structure of F-actin in the three colon cancer cells were also investigated. By using phalloidin staining and a laser confocal microscope, as shown in FIG. 1F, cytoskeleton presented well spread and extended fibrous structure in control culture. Comparing to the control, regular architecture and expression level of F-actin were found to be disrupted and decreased in response to Camphorataimide B treatments. Taken together, these results revealed that Camphoratamide B significantly inhibited adhesion, migration and invasiveness of colon cancer cells through disrupted integrity of structural cytoskeleton.

Figure 2A:
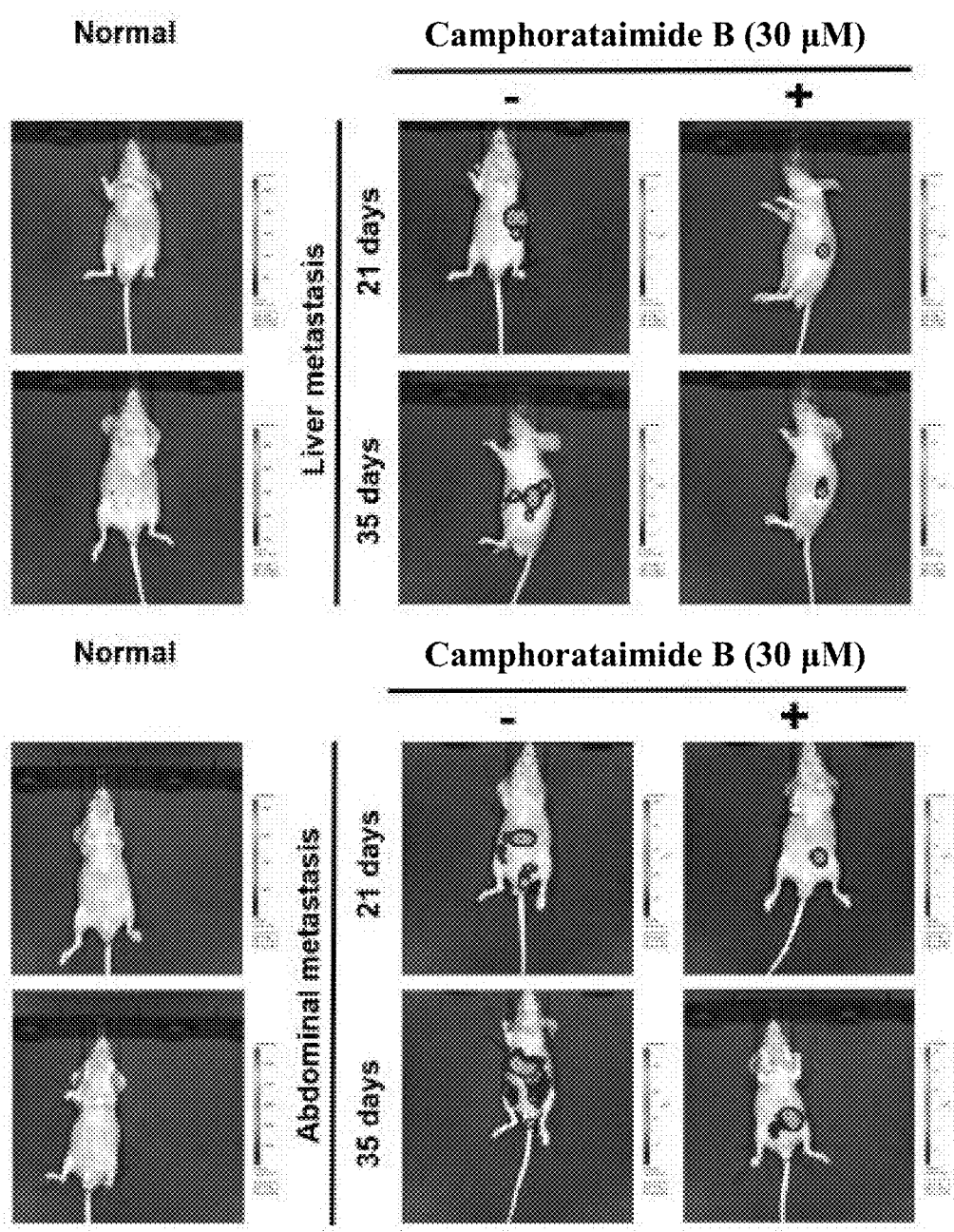
FIG. 2A: Camphorataimide B suppressed liver and abdominal metastasis of DLD-1 cells in ex vivo xenograft mice model. Luciferase expressing DLD-1 cells were pretreated with or without 30 μM Camphorataimide B for 24 hours, and then injected into the abdomen and spleen of Balb/c nude mice (five mice for each group), 35 days after implantation, the representative ex vivo images for liver and abdominal metastasis burden in xenografted animals were monitored using bioluminescent imaging (BLI).
Figure 2B:
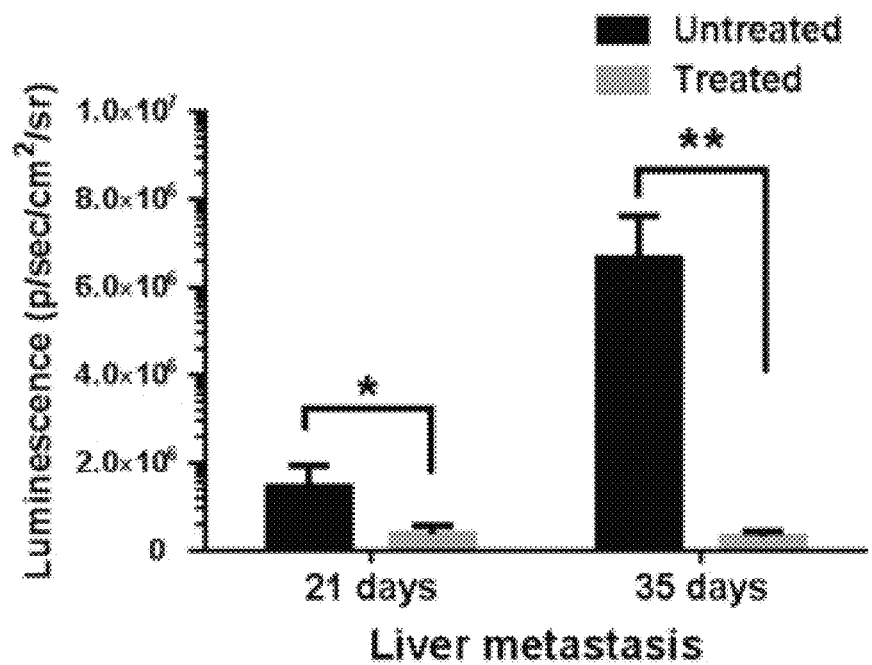
FIG. 2B: Quantitation of results of FIG. 2A. Luciferase expressing DLD-1 cells were pretreated with or without 30 μM Camphorataimide B for 24 hours, and then injected into the abdomen and spleen of Balb/c nude mice. After 35 days implantation, the mice were photographed and tumor metastatic capability was analyzed. * and ** represented P<0.01 and P<0.001 as compared to untreated group, respectively.
Figure 2B:
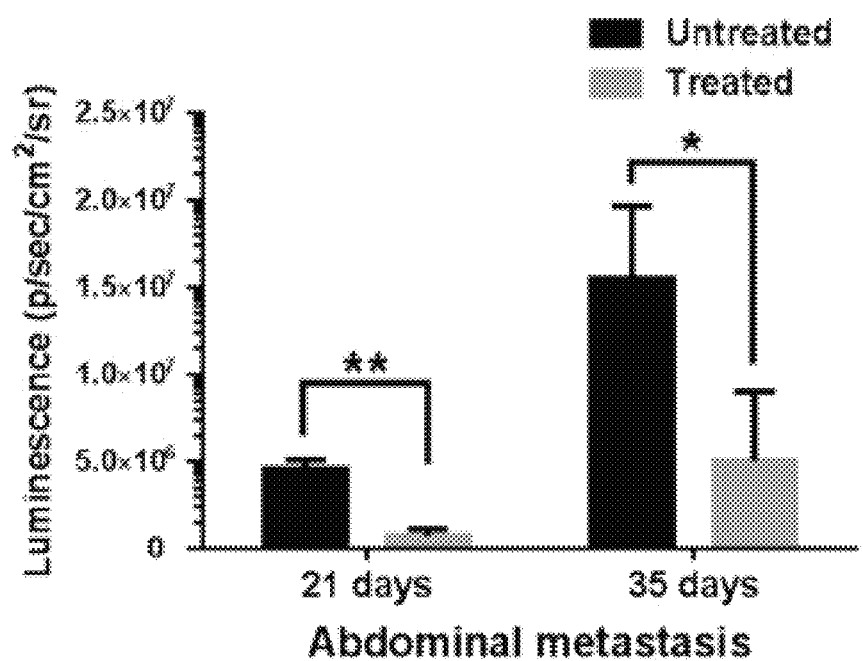
Figure 2C:
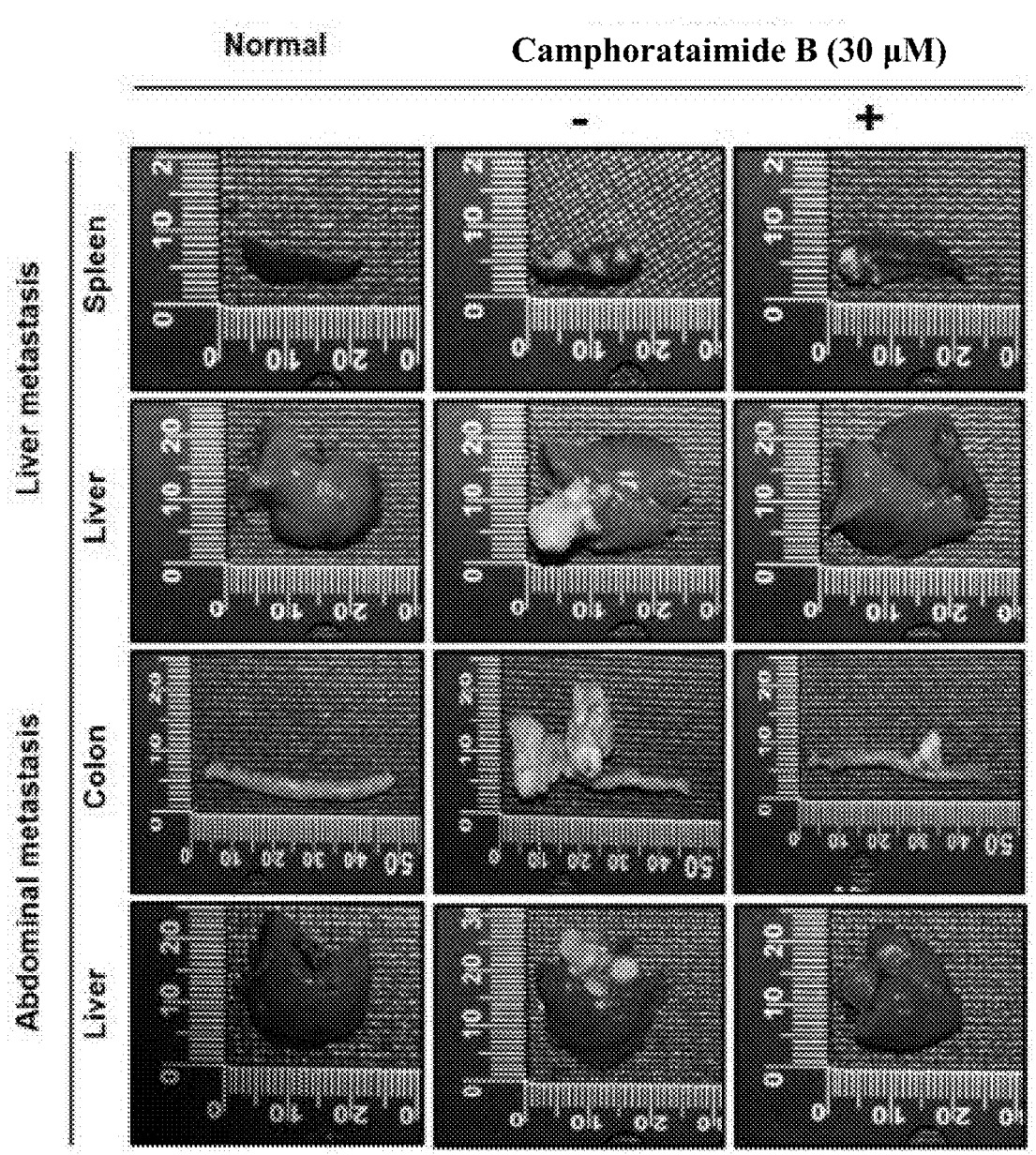
FIG. 2C: Camphorataimide B suppressed hepatic and abdominal metastasis of DLD-1 cells in ex vivo xenograft mice model. DLD-1 cells were pretreated with or without 30 μM Camphorataimide B for 24 hours, and then spleeny and intraperitoneally injected into Balb/c mice, respectively. After 35 days, the mice were sacrificed and the tissues were obtained and photographed.
Figure 2D:
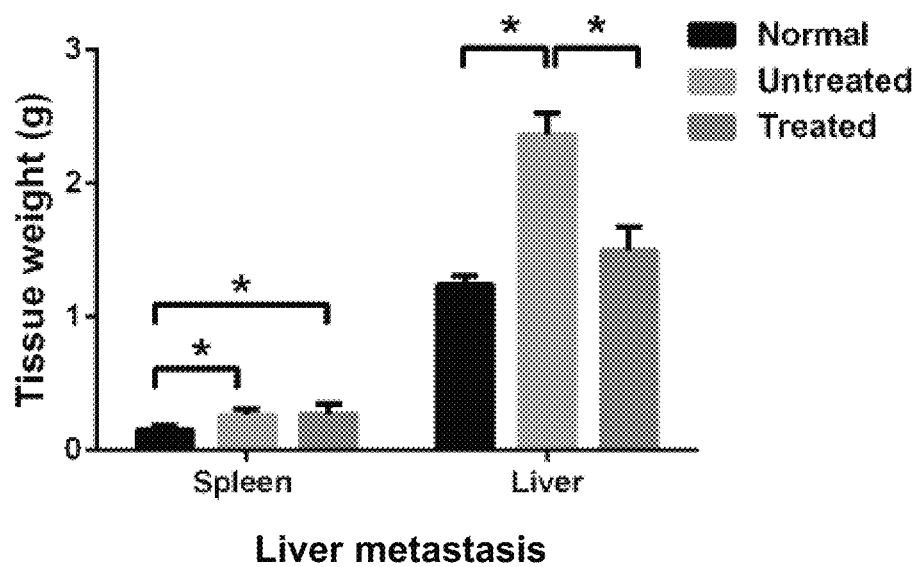
FIG. 2D: Quantitation of results of FIG. 2C. DLD-1 cells were pretreated with or without 30 μM Camphorataimide B for 24 hours, and then spleeny and intraperitoneally injected into Balb/c mice, respectively. After 35 days, the mice were sacrificed and photographed. Total weight of tumor foci from the metastatic tissues were presented and quantitated. *, P<0.01 and P<0.001 between the indicated groups.
Figure 2D:
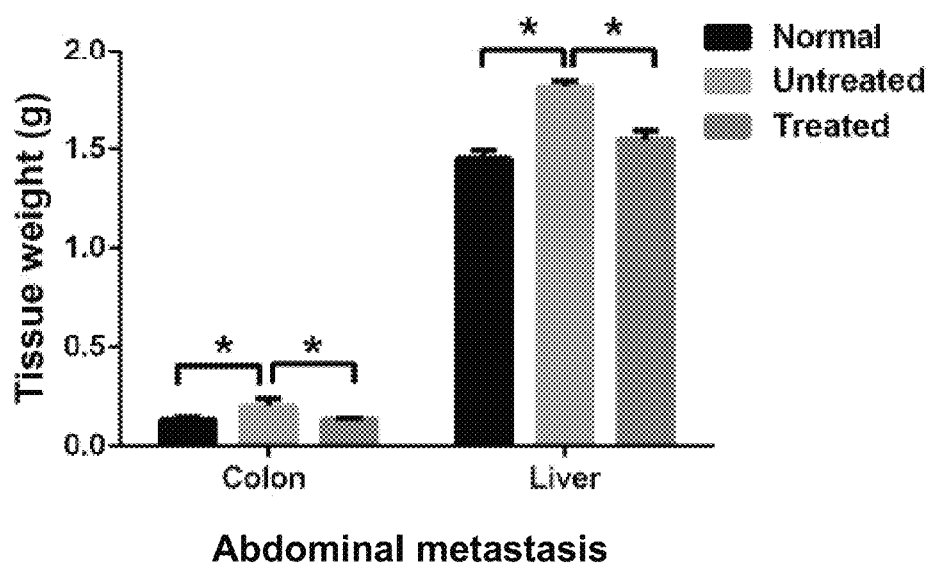
Figure 2E:
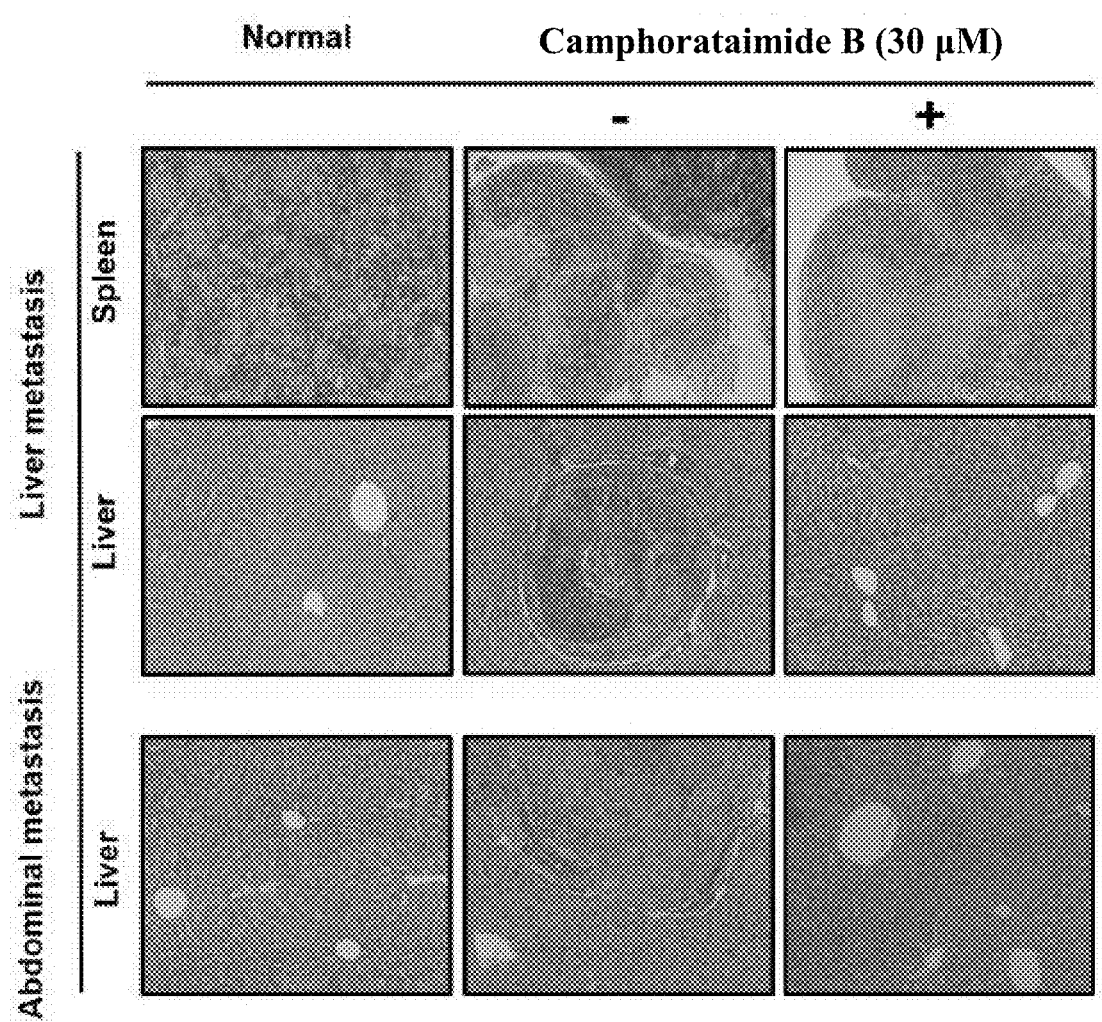
FIG. 2E: Camphorataimide B suppressed metastasis in ex vivo xenograft mice model. DLD-1 cells were pretreated with or without 30 μM Camphorataimide B for 24 hours, and then spleeny and intraperitoneally injected into Balb/c mice, respectively. Representative hematoxylin and eosin staining of spleen and liver sections were performed on day 35 after injected. 100× magnification was indicated.
Figure 2F:
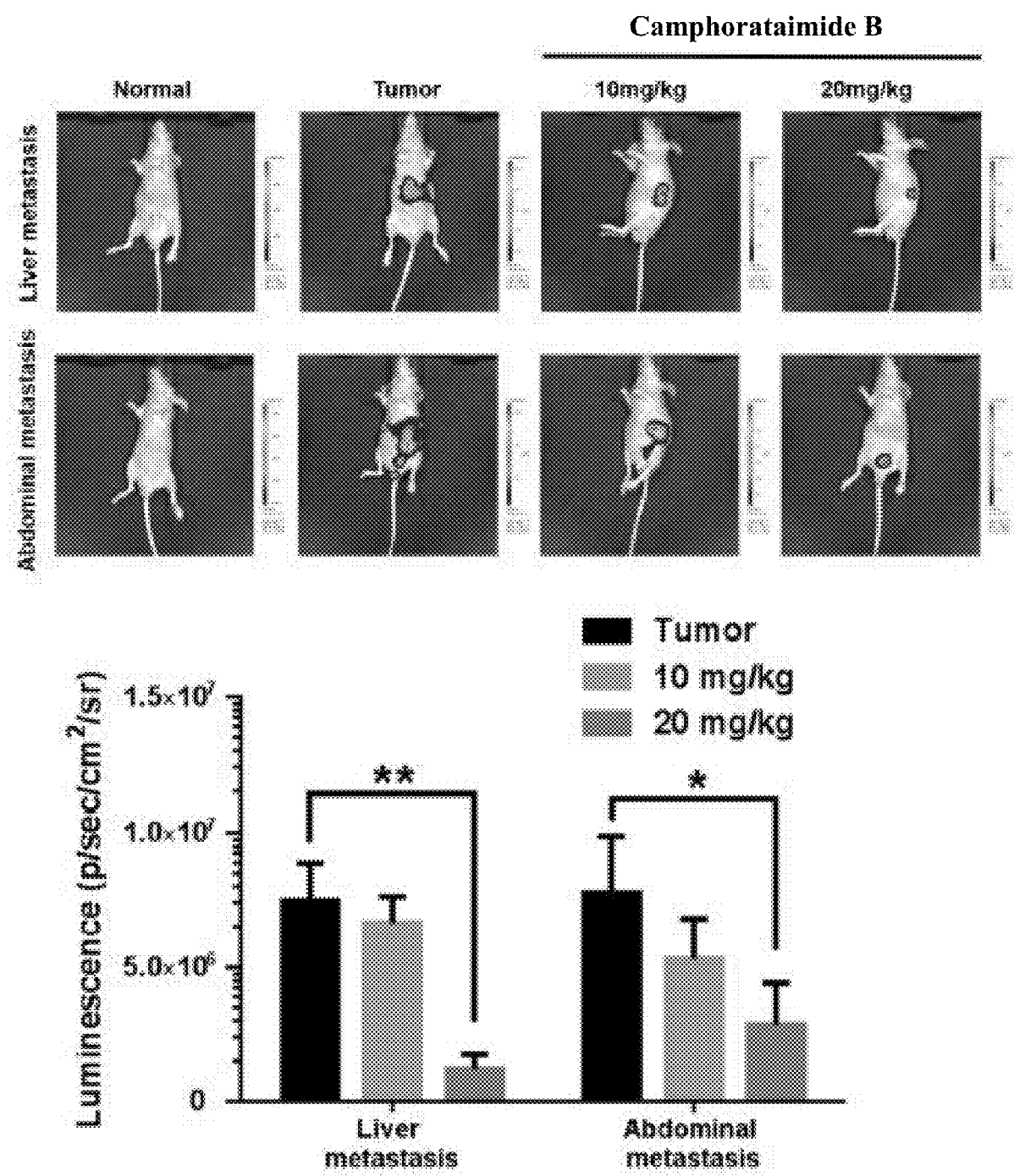
FIG. 2F: Camphorataimide B suppressed liver and abdominal metastasis of DLD-1 cells in in vivo xenograft mice model. Luciferase expressing DLD-1 cells were suspended in phosphate buffered saline and injected into the spleen and peritoneal site of 5-week-old male Balb/c nude mice, respectively. After one week, the mice were orally administrated with 10 or 20 mg/kg Camphorataimide B or saline vehicle for one month (five mice for each group). IVIS luciferase in vivo images of liver and abdominal metastasis burden were monitored using bioluminescent imaging (BLI). Data represented mean±SD. * and ** represented P<0.01 and P<0.001 between the indicated groups, respectively.
Figure 2G:
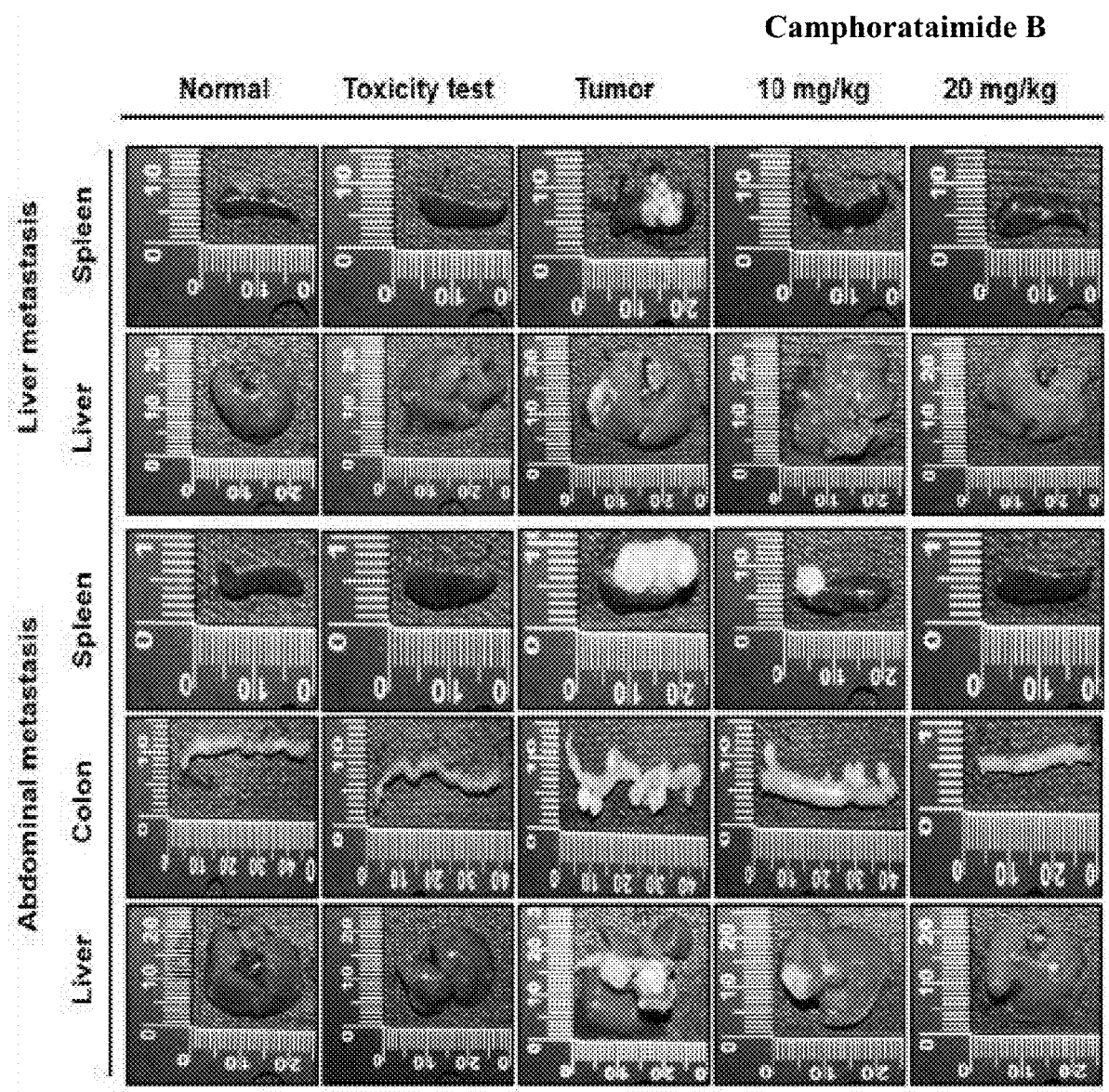
FIG. 2G: Camphorataimide B suppressed hepatic and abdominal metastasis of DLD-1 cells in in vivo xenograft mice model. Luciferase expressing DLD-1 cells were suspended in phosphate buffered saline and injected into the spleen and peritoneal site of Balb/c nude mice, respectively. After one week, the mice were orally administrated with 10 or 20 mg/kg Camphorataimide B or saline vehicle (five mice for each group). After one month, the mice were sacrificed and the tissues were obtained and photographed.
Figure 2H:
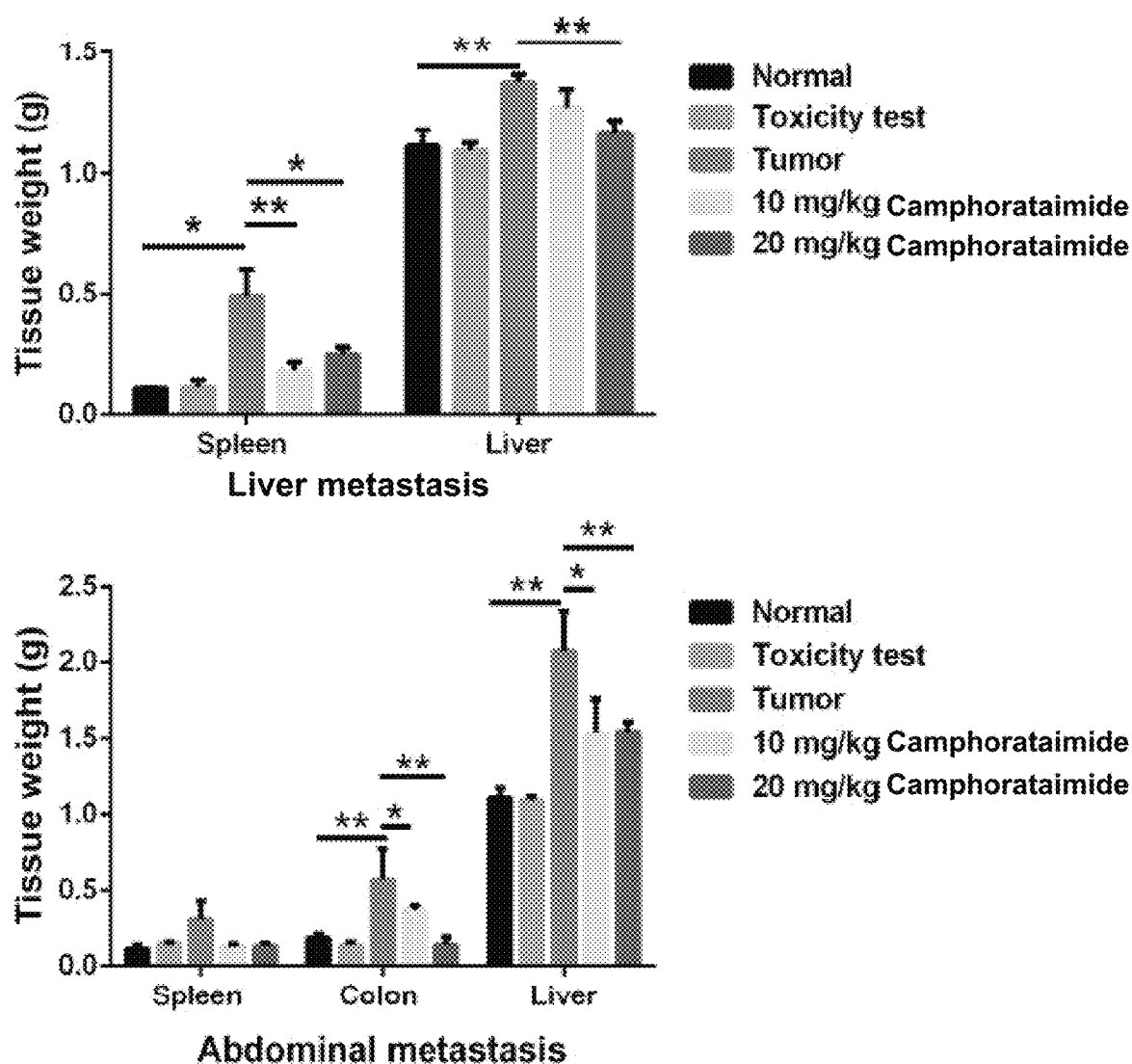
FIG. 2H: Quantitation of results of FIG. 2G. Luciferase expressing DLD-1 cells were suspended in phosphate buffered saline and injected into the spleen and peritoneal site of Balb/c nude mice, respectively. After one week, the mice were orally administrated with 10 or 20 mg/kg Camphorataimide B or saline vehicle (five mice for each group). After 35 days, the mice were sacrificed and photographed. Total weight of tumor foci from the metastatic tissues were presented and quantitated. * and ** represented P<0.01 and P<0.001 between the indicated groups, respectively.

Camphorataimide B Suppressed Liver and Abdominal Metastasis of DLD-1 Cells in Ex Vivo and In Vivo Xenograft Mice Model It had been demonstrated that Camphoratamide B suppressed adhesion, migration and invasion of DLD-1 cells in vitro according to the above results. Therefore, ex vivo and in vivo effects of Camphorataimide B treatments on tumorigenesis and metastasis by DLD-1 cells were further explored. For ex vivo xenograft mice model, Luciferase expressing-DLD-1 cells were pretreated with or without 30 μM Camphorataimide B for 24 hours, and then injected into Balb/c mice via spleen and peritoneal site. 21- and 35-days after tumor transplantation, the representative images for liver and abdominal metastatic burden in xenografted animals were monitored using bioluminescent imaging (BLI), as shown in FIGS. 2A and 2B. In another experiment, DLD-1 cells were pretreated with or without 30 μM Camphorataimide B for 24 hours, and then spleeny and intraperitoneally injected into Balb/c mice, respectively. After 35 days, the mice were sacrificed and the tissues were obtained and photographed. The results revealed that implanted DLD-1 cells strongly attached to colon tissue and formed numerous number tumors in mice. By contrast, implantation of Camphorataimide B-treated DLD-1 cells rarely attached to colon tissue and formed fewer number and smaller size of tumors (FIGS. 2C and 2D). Additionally, representative hematoxylin and eosin staining of spleen and liver sections were performed on day 35 after injected. As shown in FIG. 2E, hepatic and abdominal metastatic lesion caused by Camphorataimide B-treated DLD-1 cell was significantly diminished as compared to that by untreated cells. To determine whether Camphorataimide B can also inhibit tumor metastasis in vivo, luciferase expressing DLD-1 cells were injected into mice via spleen and intraperitoneal injection, after one week, mice were oral administered 10 and 20 mg/kg Camphorataimide B every three days for 1 month. Using bioluminescent imaging, mice receiving Camphorataimide B had smaller tumors than tumor group (FIG. 2F). After treatment, it was found that Camphorataimide B treated luciferase-expressing DLD-1 tumors grew slowly and less metastatic ability than untreated tumors (FIG. 2G). The weight of spleen and liver from xenografted animals were also measured. As expected, the increased gross weight of tumor was notably inhibited by Camphorataimide B treatment (FIG. 2H). Taken together, these results revealed that Camphorataimide B suppressed tumorigenesis and metastatic capability of colon cancer cells in vivo.

One skilled in the art readily appreciates that the present invention is well adapted to carry out the objects and obtain the ends and advantages mentioned, as well as those inherent therein. The methods and uses thereof are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for inhibiting a cancer metastasis in a subject in need thereof, comprising administering to said subject a cancer metastasis-inhibiting effective amount of: Camphorataimide B; or a composition comprising Camphorataimide B and a pharmaceutically acceptable adjuvant, vehicle, or carrier.

2. The method of claim 1, wherein the cancer is colorectal cancer.

3. The method of claim 1, wherein the subject is a mammal.

4. The method of claim 1, wherein the subject is a human.

\* \* \* \* \*